US00PP11909P2

(12) United States Plant Patent
Booman

(10) Patent No.: US PP11,909 P2
(45) Date of Patent: Jun. 5, 2001

(54) BEGONIA PLANT NAMED 'CHICAGO FIRE'

(76) Inventor: James Lawrence Booman, 2302 Bautista Ave., Vista, CA (US) 92084

( * ) Notice: Subject to any disclaimer, the term of this patent is extended or adjusted under 35 U.S.C. 154(b) by 0 days.

(21) Appl. No.: 09/375,783

(22) Filed: Aug. 17, 1999

(51) Int. Cl.[7] ..... A01H 5/00
(52) U.S. Cl. ..... Plt./343

(58) Field of Search ..... Plt./343

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Rex Begonia plant named 'Chicago Fire', characterized by its uniform growth habit; moderate plant vigor; no requirement for winter dormancy; and interesting and attractive leaf coloration and pattern.

1 Drawing Sheet

BACKGROUND OF THE INVENTION

The present invention relates to a new and distinct cultivar of Begonia plant, botanically known as *Begonia rex* hybrid, commercially known as Rex Begonia, and hereinafter referred to by the name 'Chicago Fire'.

The new Rex Begonia was discovered and selected by the Inventor in a controlled environment in Vista, Calif., in 1995, within a large group of seedling progeny from multiple crossings of unidentified selections of *Begonia rex* hybrids.

The selection of the plant was based on its uniform growth habit, moderate plant vigor, salt tolerance and attractive foliage coloration and pattern.

Asexual reproduction of the new Rex Begonia by leaf cuttings taken in a controlled environment in Vista, Calif., has shown that the unique features of this new Rex Begonia are stable and reproduced true to type in successive generations.

SUMMARY OF THE INVENTION

The cultivar 'Chicago Fire' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Chicago Fire'. These characteristics in combination distinguish 'Chicago Fire' as a new and distinct Rex Begonia:

1. Uniform growth habit.

2. Moderate plant vigor.

3. Does not require winter dormancy.

4. Interesting and attractive leaf coloration and pattern.

In side-by-side comparisons conducted by the Inventor in Vista, Calif., plants of the new Rex Begonia differ from plants of the nonpatented cultivar 'Merry Christman Corkscrew' in the following characteristics:

1. Plants of the new Rex Begonia have larger and flatter leaves than plants of the cultivar 'Merry Christmas Corkscrew'.

2. Leaves of plants of the new Rex Begonia and the cultivar 'Merry Christmas Corkscrew' differ in coloration and pattern.

3. Leaves of plants of the new Rex Begonia do not have a "corkscrew" formation whereas leaves of plants of the cultivar 'Merry Christmas Corkscrew' have a "corkscrew" formation.

4. Plants of the new Rex Begonia do not require a winter dormancy period whereas plants of the cultivar 'Merry Christmas Corkscrew' do require a winter dormancy period.

In side-by-side comparisons conducted by the Inventor in Vista, Calif., plants of the new Rex Begonia differ from plants of the nonpatented cultivar 'Lillium' in the following characteristics:

1. Plants of the new Rex Begonia have more rounded and flatter leaves than plants of the cultivar 'Lillium'.

2. Leaves of plants of the new Rex Begonia and the cultivar 'Lillium' differ in coloration and pattern.

3. Plants of the new Rex Begonia do not require a winter dormancy period whereas plants of the cultivar 'Lillium' do require a winter dormancy period.

BRIEF DESCRIPTION OF THE PHOTOGRAPH

The accompanying colored photograph illustrates the overall appearance of the new Rex Begonia, showing the colors as true as it is reasonably possible to obtain in colored reproductions of this type. The photograph comprises a top perspective view of a typical plant of 'Chicago Fire'. Foliage colors in the photograph may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown during the spring in Vista, Calif., under conditions which approximate commercial practices. Plants used for this description were grown in 15-cm containers for about 3 months.

Botanical classification: *Begonia rex* hybrid cultivar 'Chicago Fire'.

Commercial classification: Rex Begonia.

Parentage: Chance seedling of multiple crossings of unidentified selections of *Begonia rex* hybrids.

Propagation:

*Type.*—Leaf cuttings.

*Time to initiate roots, summer.*—About 56 days at 21° C.

*Time to initiate roots, winter.*—About 56 days at 21° C.

*Time to develop roots, summer.*—About 84 days at 21° C.

*Time to develop roots, winter.*—About 98 days at 21° C.

*Rooting habit.*—Fine, fibrous and well-branched.

Plant description:

*Plant form.*—Rosette; compact; outwardly arching potted plant; freely basal branching with good leaf petiole strength.

*Vigor.*—Moderate.

*Plant height, soil surface to top of leaf canopy.*—About 27 cm.

*Plant width.*—About 58 cm.

*Leaves.*—Arrangement: Simple. Length: Petiole to apex: About 16 cm. Base to apex: About 20 cm. Width: About 15.2 cm. Shape: Asymmetrical, oblique. Apex: Acute. Base: Overlapping cordate. Margin: Slightly pectinate; irregularly undulate. Texture: Leathery, rugose; pubescence on lower surface veins. Color: Young foliage, upper surface: Margin: 187A, close to 202A. Central venal areas: 187A, close to 202A. Blade: Metallic 59A, expanding to 59B to 59C then merging with 196A. Antemarginal: Thin border of 147A to 147B. Young foliage, lower surface: Margin: 187A. Central venal areas: 187A, close to 202A at center. Background: 195A to 195B. Mature, fully expanded, foliage, upper surface: Margin: Dark brown, close to 202A, slight overtones of 187A. Central venal areas: Close to 202A. Blade: Metallic, close to 187A. Background, antemarginal: Close to 202A; slight overtones of 147A; some blisters of metallic 187A. Veins: Close to 183A. Mature, fully expanded, foliage, lower surface: Margin: 187A. Central venal area: 187A. Background: 138B. Veins: 183B; reticulate.

*Petioles.*—Length: About 20.5 cm. Diameter: About 7 mm. Shape: Canaliculate. Texture: Pubescent. Color: 183A to 184B.

*Stipules.*—Length: About 8 mm. Diameter at base: About 5.5 mm. Shape: Subulate, close to lanceolate. Color: Close to 178A to 179A.

Flower description:

*Flowering habit.*—Male flowers, single with one whorl of four tepals. Female flowers, semi-double with three tepals interior to outer whorl of five tepals. Usually about three or four flowers per cyme. Flowers persistent.

*Natural flowering season.*—Plants will flower continuously, but typically plants flower more abundantly during the spring and summer.

*Flowers.*—Shape: Rounded; somewhat cup-shaped. Diameter: About 3.7 cm. Depth (height): About 2.1 cm. Aspect: Drooping about 60° from vertical. Fragrance: None.

*Flower buds.*—Shape: Ovoid; bulbous with marginal lip. Length: About 13.5 mm. Diameter: About 9 mm. Color: 68C.

*Tepals.*—Arrangement: Rosette. Length: About 3.4 cm. Width: About 3.3 cm. Shape: Ovate with obtuse apex. Margin: Entire. Texture: Smooth, waxy; iridescent, translucent. Color: When opening, upper surface: 55C. When opening, lower surface: 55C. Fully opened, upper surface: Iridescent, 55C. Fully opened, lower surface: 55B.

*Peduncles.*—Angle: About 25° from vertical. Length: About 6 cm. Diameter: About 2 mm. Strength: Firm. Texture: Smooth, waxy. Color: 172A.

*Pedicles.*—Angle: About 45° from vertical. Length: About 2 cm. Diameter: About 2 mm. Strength: Moderate. Texture: Smooth, waxy. Color: 172A.

*Reproductive organs.*—Male flowers: Stamen quantity: About 97; globose mass. Anther shape: Rhomboidal. Anther length: About 2 mm. Filament length: About 1 mm. Anther color: Close to 22A. Pollen: Not observed. Female flowers: Pistil length: About 2 cm. Stigma shape: Funnel; bilobate. Stigma color: 31A; margin, 26A to 26B. Ovary: Inferior; three-winged; one large top wing and two lower wings both surfaces; 179A to 199A.

Disease resistance: Resistance to diseases common to Rex Begonia has not been determined.

Seed production: Seed production has not been observed.

It is claimed:

1. A new and distinct cultivar of Rex Begonia plant named 'Chicago Fire', as illustrated and described.

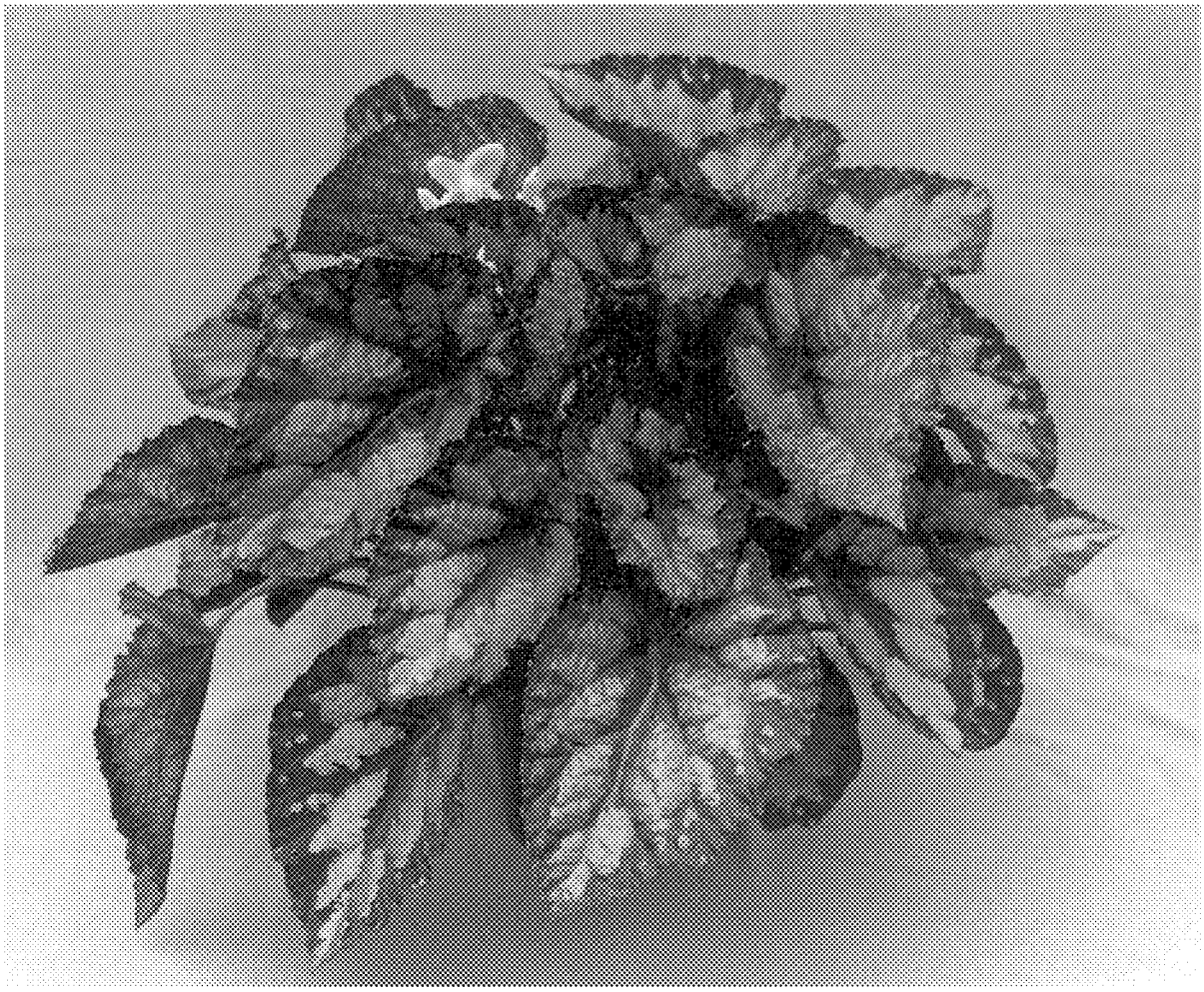

* * * * *